United States Patent [19]
Edelman et al.

[11] Patent Number: 5,985,822
[45] Date of Patent: *Nov. 16, 1999

[54] INHIBITION OF GLIAL CELL PROLIFERATION WITH N-CAM HOMOPHILIC PEPTIDES

[75] Inventors: Gerald M. Edelman, La Jolla; Kathryn L. Crossin, San Diego; Olaf Sporns, San Diego; Leslie Krushel, San Diego, all of Calif.

[73] Assignee: The Scripps Research Institute, La Jolla, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/440,725

[22] Filed: May 8, 1995

Related U.S. Application Data

[63] Continuation-in-part of application No. 08/353,658, Dec. 9, 1994, abandoned.

[51] Int. Cl.⁶ .............................. A61K 38/00; C07K 5/00
[52] U.S. Cl. ................. 514/2; 514/15; 530/300; 530/327; 530/328; 530/350
[58] Field of Search ................. 435/375; 514/2, 514/8, 12–16; 530/300, 327, 350, 328

[56] References Cited

PUBLICATIONS

Barrett, C. P. et al. (1984) *Exp. Neurol.* 84, 374–385.
Bickel, U. et al. (1993) *Proc. Natl. Acad. Sci. USA* 90 2618–2622.
Crossin, K. L. (1991) *Proc. Natl. Acad. Sci. USA* 88, 11403–11407.
Cunningham, B. A. et al. (1987) *Science* 236, 799–806.
Daniloff, J. K. et al. (1986) *J. Cell Biol.* 103, 929–945.
Doherty, P. & Walsh, F. S. (1994) *Current Opinion in Neurobiology* 4, 49–55.
Edelman, G. M. (1986) *Ann. Rev. Cell Biol.* 2, 81–116.
Flanders, K. C. et al. (1991) *Development* 113, 183–191.
Gasser, U. E. & Hatten, M. E. (1990) *J. Neurosci.* 10, 1276–1285.
Gerdes, W. et al. (1992) *NeuroReport* 3, 43–46.
Hatten, M. E. (1987) *J. Cell. Biol.* 104, 1353–1360.
Hemperly, et al. (1986) *Proc. Natl. Acad. Sci. USA* 83, 3037–3041.
Hoffman, S. et al. (1982) *J. Biol. Chem.* 257, 7720–7729.
Hunter, K. E., et al. (1993) *Glia* 7, 203–211.
Krushel, L.A., et al. (1995) *Proc. Natl. Acad. Sci. USA* 92, 4323–4327.
Ludwin, S. K. (1984) *Nature* 308, 274–275.
Murray, et al., (1986) *J. Cell Biology* 102: 189–193.
Rao et al., (1992) *J. Cell Biology* 118: 937–949.
Rao et al., (1993) *J. Biological Chemistry* 268: 20630–20638.
Sandig, M., et al (1994) *J. Biol. Chem.* 269, 14841–14848.
Searle, P.F. et al. (1985) *Molec. & Cell. Biol.* 5, 1480–1489.
Small, S. J., Shull, G. E., Santoni, M. J. & Akeson, R. (1987) *J. Cell. Biol.* 105, 2335–2345.
Brackenbury, R. et al., (1977) *J. Biol. Chem.* 252, 6835–6840.
Frei et al, *J. Cell. Biol.*(USA) 118(1): 177–194, 1992.
Barinago et al, *Science* 264:772–774, 1994.
Rudinger, "Peptide Hormones" Published by University Park Press, Jun. 1976, pp. 1–6.
Bargess et al, *Journal of Cell Biology* 111:2129–2138, 1990.
Lazar et al, *Molecular and Celluar Biology*, 8(3):1247–1252, 1988.

*Primary Examiner*—Patricia A. Duffy
*Attorney, Agent, or Firm*—Thomas Fitting; Emily Holmes

[57] ABSTRACT

Methods and compositions are disclosed that are useful for the inhibition of glial cell proliferation by means of binding inhibiting agents to neural cell adhesion (N-CAM) molecules present on the cell surface. Such inhibiting agents can be peptides derived from the homophilic binding region of N-CAM, monoclonal antibodies, polyclonal antibodies, Fab' fragments, and the like. Exemplary N-CAM homophilic peptides are 7 to 90 amino acid residues having a positively charged amino acid residue separated from a negatively charged amino acid residue by five intervening amino acid residues.

25 Claims, 8 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (xi) SEQUENCE DESCRIPTION: SEQ ID NO:1:

Lys Tyr Ser Phe Asn Tyr Asp Gly Ser Glu
1          5                  10

(2) INFORMATION FOR SEQ ID NO:2:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (xi) SEQUENCE DESCRIPTION: SEQ ID NO:2:

Lys His Ile Phe Ser Asp Asp Ser Ser Glu
1               5                   10

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:3:

AGAUCCUUAG UUCGCAGCAU UGUA                                              24

(2) INFORMATION FOR SEQ ID NO:4:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

GTGCGTGCCA GGCAGAGCAC TATGAACGCC ACTGCCAACC TCAGCCAGTC TGTCACCTTA        60
GCATGTGATG CTGATGGCTT TCCTGAGCCA ACCATGACGT GGACAAAGGA TGGAGAGCCA       120
ATAGAGCAGG AGGATAACGA AGAGAAATAC AGTTTTAACT ACGATGGGTC CGAGCTGATC       180
ATCAAGAAGG TGGATAAGAG TGACGAAGCA GAGTACATCT GCATCGCTGA GAACAAGGCT       240
GGCGAGCAGG ATGCCACCAT TCATCTCAAA GTCTTTGCAA AA                          282

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

ATATGTGGAT CCCTATTTTG CAAAGAC                                           27

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

ATGTACCCAT CGGCGTGCGT GCCAGG                                           26

(2) INFORMATION FOR SEQ ID NO:7:

(i) SEQUENCE CHARACTERISTICS:
            (A) LENGTH: 334 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

ATGTACCCAT GGGCGTGCGT GCCAGGCAGA GCACTATGAA CGCCACTGCC AACCTCAGCC       60

AGTCTGTCAC CTTAGCATGT GATGCTGATG GCTTTCCTGA GCCAACCATG ACGTGGACAA      120

AGGATGGAGA GCCAATAGAG CAGGAGGATA ACGAAGAGAA ATACAGTTTT AACTACGATG      180

GGTCCGAGCT GATCATCAAG AAGGTGGATA AGAGTGACGA AGCAGAGTAC ATCTGCATCG      240

CTGAGAACAA GGCTGGCGAG CAGGATGCCA CCATTCATCT CAAAGTCTTT GCAAAACCCA      300

AAATCACATA TGTGGATCCC TATTTTGCAA AGAC                                 334

(2) INFORMATION FOR SEQ ID NO:8:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:8:

Gly Phe Asn Ser Ser Tyr Glu Asp Tyr Lys
1               5                   10

(2) INFORMATION FOR SEQ ID NO:9:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (xi) SEQUENCE DESCRIPTION: SEQ ID NO:9:

Ser Phe Ser Ile Ser Asp Glu Asp His Lys
1               5                   10

(2) INFORMATION FOR SEQ ID NO:10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: mRNA (iii) HYPOTHETICAL: NO (iv) ANTI-SENSE: YES (xi) SEQUENCE DESCRIPTION: SEQ ID NO:10:

GUCCAUGUAC AUCUAGUCAG UUGA                24

INHIBITION OF GLIAL CELL PROLIFERATION WITH N-CAM HOMOPHILIC PEPTIDES

CROSS-REFERENCE TO RELATED APPLICATION

This application is a continuation-in-part of U.S. patent application Ser. No. 08/353,658, filed December 9, 1994 now abandoned.

GOVERNMENTAL RIGHTS

This invention was made with governmental support from the United States Government, National Institutes of Health, Grant HD09635; the United States Government has certain rights in the invention.

FIELD OF INVENTION

The invention relates to methods and compositions suitable for inhibiting glial cell proliferation. The invention relates to the use of peptides, antibodies and oligonucleotides for inhibiting glial cell proliferation. More particularly, the invention relates to peptides comprising at least part of the amino acid sequence of neural cell adhesion molecule (N-CAM) and to compositions that utilize these peptides to inhibit DNA synthesis and cell division of glial cells.

BACKGROUND

During embryogenesis, the proliferation of glioblasts and their differentiation into several glial cell types appear to be closely coordinated with the development of neurons. During early postnatal development of the brain, glial cell proliferation continues at significant levels after neuronal proliferation has mostly ceased. In general, glial cell proliferation in the brain remains strongly inhibited throughout adult life, except in tumorigenesis and after injury.

The control of glial cell proliferation is an important factor in the regulation of neural development, regeneration, and tumorigenesis. The experiments described herein provide evidence for a new functional role of N-CAM in the control of glial cell proliferation in vitro and in vivo.

After physical injury to the central nervous system (CNS), astrocytes respond by changes in cell morphology, increased expression of glial fibrillary acidic protein (GFAP), hypertrophy, and rapid proliferation (Ludwin, S. K. (1984) *Nature* 308, 274–275). Such reactive astrocytes form glial scars in a process of gliosis that appears to interfere with neuronal regeneration in the adult CNS (Barrett, C. P. et al. (1984) *Exp. Neurol.* 84, 374–385; Reier, P. J. & Houle, J. D. (1988) *In Advances in Neurology,* (Waxman, S. G., ed.). Raven Press, New York, pp. 87–138).

Glial cell proliferation can be influenced by a variety of factors. Stimulatory effects are exerted by various growth factors (Kniss, D. A. & Burry, R. W. (1988) *Brain Res.* 439, 281–288), interleukin-6 (IL-6) (Selmaj, K. W. et al. (1990) *J. Immunol.* 144, 129–135), interleukin-1β (IL-1β) (Giulian, D. & Lachman, L. B. (1985) *Science* 228, 497–499), tumor necrosis factor (Barna, B. P. et al. (1990) *J. Neuroimmunol.* 30, 239–243) and γ-interferon (Yong, V. et al. (1991) *Proc. Natl. Acad. Sci. USA* 88, 7016–7020). The mitogenic effects of several of these factors can be inhibited by transforming growth factor-β (Hunter, K. E., Sporn, M. B. & Davies, A. M. (1993) *Glia* 7, 203–211) which is produced by neurons (Flanders, K. C. et al. (1991) *Development* 113, 183–191).

Further evidence points to a direct involvement of neurons in the control of glial cell proliferation. The addition of purified cerebellar granule neurons to cerebellar astrocytes (Hatten, M. E. (1987) *J. Cell Biol.* 104, 1353–1360) or of hippocampal neurons to glia (Gasser, U. E. & Hatten, M. E. (1990) *J. Neurosci.* 10, 1276–1285) resulted in a decrease in glial cell proliferation. This inhibition depends on a proper ratio of neurons to glia of about 4 to 1, ensuring that astrocytes make surface contact with the added neurons. A cell membrane preparation of cerebellar granule neurons also inhibited proliferation, while medium conditioned by such neurons did not, indicating that membrane-associated molecules might be involved in the neuronal control of glial cell proliferation.

N-CAM (Edelman, G. M. (1986) *Ann. Rev. Cell Biol.* 2, 81–116; Cunningham, B. A. et al. (1987) *Science* 236, 799–806) has an important regulatory role in the developing nervous system and is present in adult nervous tissue. While the traditional view centers in the role of N-CAM in providing adhesion to the substrate and other cells, there is evidence that N-CAM can mediate signalling across the cell membrane in N-CAM mediated neurite outgrowth (Doherty, P. & Walsh, F. S. (1994) *Current Opinion in Neurobiology* 4, 49–55).

Astrocytes express a variety of adhesion molecules, among them the cell adhesion molecules N-CAM, and L1, and the extracellular matrix protein laminin. N-CAM has been found in astrocytes in vivo (Bartsch, U. et al. (1989) *J. Comp. Neurol.* 284, 451–462) as well as in primary astrocyte cultures (Noble, M. et al. (1985) *Nature (London)* 316, 725–728) although normal levels of N-CAM in glia are low in comparison to those in neurons (Nybroe, O. et al. (1985) *J. Cell. Biol.* 101, 2310–2315). The amount of N-CAM expressed on the surface of astrocytes (Smith, G. M. et al. (1993) *J. Neurochem.* 60, 1453–1466) as well as in the nervous system as a whole (Chuong, C.-M. & Edelman, G. M. (1984) *J. Neurosci.* 4, 2354–2368; Linnemann, D. et al. (1993) *Int. J. Devl. Neurosci.* 11, 71–81) decreases significantly as the CNS matures as compared to the amounts seen in prenatal and early postnatal development.

Levels of N-CAM have been shown to change after injury to nervous tissue. For example, after neurotoxin-induced brain damage, glial cells re-express high levels of the highly sialylated embryonic form of N-CAM (Le Gal La Salle, G. et al. (1992) *J. Neurosci.* 12, 872–882). Peripheral nerve injury leads to the expression of high levels of sialic-acid rich N-CAM in both neural and glial tissue (Daniloff, J. K. et al. (1986) *J. Cell Biol.* 103, 929–945). The increased expression of N-CAM after injury and the presence of N-CAM on reactive astrocytes indicates that cell adhesion molecules may play a functional role in regeneration and potential healing after such insults.

Renewed glial cell proliferation and gliosis are important in the response of neural tissue to injury. A reduction in the amount of gliosis after CNS injury may be a significant factor in permitting axonal regeneration across a lesion site. Neuronal regeneration in the adult CNS can occur if regenerating axons are presented with an appropriate environment (Aguayo, A. J. (1985) *In Synaptic plasticity,* (Cotman, C. W., ed.). Guilford, New York, pp. 457–484). Injury to the CNS of neonatal rats results in less extensive gliosis as compared to the adult (Barrett et al. 1984) possibly facilitating neuronal regeneration. Moreover, gliosis in the adult can be reduced by transplantation of immature astrocytes into the lesion site (Smith, D. B. & Johnson, K. S. (1988) *Gene* 67, 31–40). Our experiments raise the possibility that this might be due to the high levels of N-CAM expressed by immature astrocytes. Further elucidation of these responses and definition of the signalling pathways that mediate the inhibition of glial cell proliferation facilitate the design of rational therapies to enhance regeneration by CNS neurons.

SUMMARY OF THE INVENTION

The present invention provides a method as well as a composition suitable for inhibiting glial cell proliferation. To this end, a mixed population of neural cells and glial cells is exposed to peptides that interact with N-CAM. The present invention also provides a method for identifying populations of glial cells susceptible to proliferation inhibition as well as a method for enriching a mixed population of glial and neural cells in glial cells susceptible to proliferation inhibition. The present invention contemplates the inhibition of the proliferation of cells: any cell having N-CAM on the cell surface is suitable for the practice of the invention.

The present invention provides, in general, a method of inhibiting proliferation of cells having neural cell adhesion molecule (N-CAM) on the cell surface. Proliferation of such cells can be inhibited by contacting the cells with an proliferation inhibiting amount of a N-CAM homophilic peptide having at least 7 amino acid residues, preferably 7 to 90 amino acid residues. Such N-CAM homophilic peptides include a positively charged amino acid residue spaced from a negatively charged amino acid residue, the positively charged amino acid residue being separated from the negatively charged amino acid residue by five intervening amino acid residues.

Detailed Description

Figures 1A, 1B, 1C:
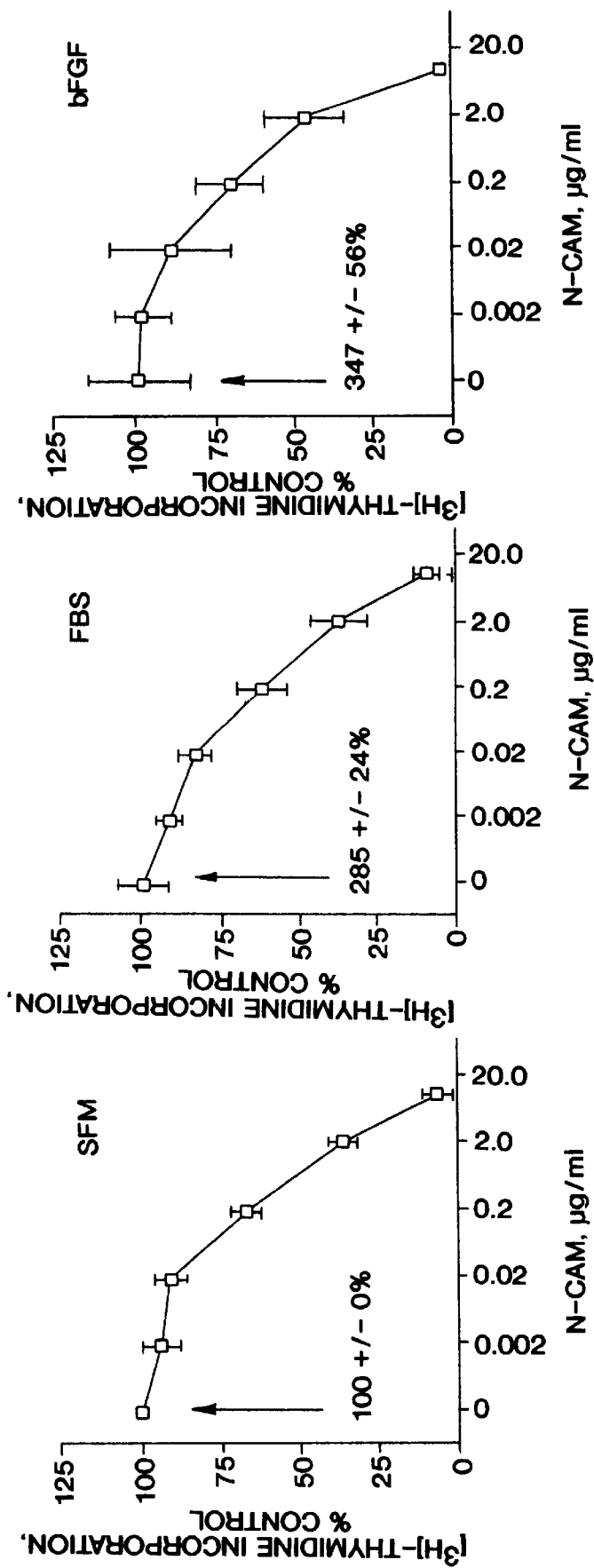
FIG. 1: Inhibition of proliferation as a function of the amount of N-CAM present in the medium for different culture conditions: (A) SFM (n=10), (B) SFM plus 1% FES (n=5), (C) SFM plus 20 ng/ml bFGF (n=5). The number in the upper left hand corner gives the level of [$^3$H]-thymidine incorporation (percent of SFM control) with no N-CAM added. Throughout the paper, [$^3$H]-thymidine incorporation is normalized relative to [$^{35}$S]-methionine cell labeling, calculated as the ratio [$^3$H]dpm/[$^{35}$S]dpm and expressed as a percentage (mean ±S.E.M.) of the respective control (no N-CAM added) for each of the three conditions. Cell density is $7 \times 10^4$ cells/cm$^2$ throughout.

Abbreviations:

| | |
|---|---|
| bFGF | basic fibroblast growth factor |
| FBS | fetal bovine serum |
| FITC | fluorescein isothiocyanate |
| GFAP | glial fibrillary acidic protein |
| N-CAM | neural cell adhesion molecule |
| PBS | phosphate buffered saline |
| SFM | serum free medium |

Cell proliferation, comprising growth and reproduction of cells, is a key primary process not only during neural development but also in the regenerative response of neural tissue to injury. Proliferation of the glial cells of neural tissue has been reported to be controlled, at least in part, by a neuronal signal that may involve cell surface molecules.

N-CAM, as well as peptides comprising a portion of the amino acid sequence of N-CAM and including the homophilic binding region (herein termed N-CAM homophilic peptides), are capable of inhibiting glial cell proliferation. The addition of soluble N-CAM portions to primary cultures of astrocytes inhibits their proliferation. This inhibitory effect is believed to be mediated by homophilic N-CAM binding. This inhibitory effect can be elicited by addition of short synthetic peptides with sequences corresponding to parts of the third immunoglobulin-like domain of N-CAM.

It has recently been found that N-CAM inhibits glial cell proliferation of both astrocytes in vitro and brain glial cells in vivo. This inhibitory effect has been elicited in primary cultures of rat forebrain astrocytes grown in chemically defined serum free medium or in a medium that had been supplemented with growth factors. The present invention provides methods of using N-CAM and related molecules to control glial cell proliferation. The present invention is suitable for controlling the formation of glial scars after central nervous system injury, which may in turn aid neuronal regeneration. The inhibitory effect on proliferation of short synthetic peptides with sequences located in the third immunoglobulin-like domain of N-CAM lends additional support to the hypothesis that N-CAM homophilic binding can lead to decreased proliferation. This result suggests that binding to this region of N-CAM is sufficient to elicit a signal leading to an intracellular response. Although any influence of such peptides on cell proliferation has not been reported previously, it has been shown that the decapeptide sequence KYSFNYDGSE (SEQ ID NO 1) is directly involved in chick N-CAM homophilic binding (Rao et al., 1992). In solution, this peptide disrupted N-CAM-homophilic binding and inhibited N-CAM-dependent neurite outgrowth from retinal cells (Sandig, M., et al. (1994) *J. Biol. Chem.* 269, 14841–14848).

Such decapeptides inhibit glial cell proliferation and can mimic the effect of whole purified N-CAM. These peptides comprise a portion of the amino acid sequence of N-CAM and include the homophilic binding region as N-CAM homophilic peptides. Binding of such peptides to N-CAM is sufficient to elicit a signaling event across the cell membrane.

The magnitude of the inhibitory effect of N-CAM was dependent on cell density: it was maximal at low cell densities and weakened progressively as cells approached confluency. Synthetic N-CAM homophilic peptides mimicked the effect of purified N-CAM, while peptides of the same length and amino acid composition but with a randomized sequence did not. The addition of N-CAM antisense oligonucleotides to astrocyte primary cultures for 48 hours resulted in reduced levels of N-CAM expression. After N-CAM levels on astrocytes were diminished by this treatment, the anti-proliferative effect of N-CAM added to the medium was significantly reduced. These results indicate that N-CAM homophilic peptides may be used to control proliferation of glial cells.

The experimental results indicate that the proliferation of rat forebrain astrocytes in primary culture can be strongly inhibited by addition of purified N-CAM to the culture medium. The proliferation of other cell types expressing N-CAM also seem to be susceptible to N-CAM mediated inhibition. It has recently been found that C6 glioma cells which express N-CAM on their cell surface also decrease their rate of proliferation in response to externally added N-CAM when grown in SFM at low cell densities. An assay for the presence of N-CAM on the cell surface helps to predict the ability of N-CAM homophilic peptides to inhibit the proliferation of a cell type.

The effect on astrocytes is mimicked by polyclonal N-CAM antibodies and N-CAM Fab' fragments. These findings indicate that the inhibition of proliferation does not result from crosslinking of N-CAM at the cell surface, but is the result of a signal mediated by homophilic binding to N-CAM at the glial surface. This conclusion is also supported by the finding that N-CAM peptides can have the same effect. The results of antisense experiments indicate that a threshold amount of N-CAM at the glial surface is required.

N-CAM homophilic peptides or N-CAM homophilic antibodies are useful agents for inhibiting the proliferation of glial cells in a mixed culture of glial and neural cells when the desired goal is culturing neural cells free of glial cell contamination.

A suitable N-CAM homophilic decapeptide contemplated by the present invention is described by the formula:

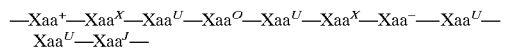

where $Xaa^+$ is an amino acid residue with a positively charged side chain, $Xaa^J$ is an amino acid residue with a nonpositive side chain, $Xaa^O$ is an amino acid residue with a nonpolar side chain, $Xaa^U$ is an amino acid residue with an uncharged side chain, $Xaa^X$ is an amino acid residue with no specific constraints on the nature of the side chain, and $Xaa^-$ is an amino acid residue with a negatively charged side chain. A suitable N-CAM homophilic is heptapeptide is described by the formula:

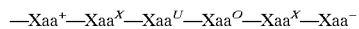

A preferred N-CAM homophilic decapeptide contemplated by the present invention is described by the formula:

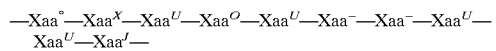

A preferred N-CAM homophilic heptapeptide contemplated by the present invention is described by the formula:

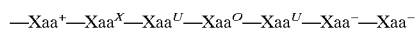

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

An antibody composition of the present invention is characterized as containing antibody molecules that immunoreact with N-CAM peptides or portions thereof.

An antibody composition of the present invention is typically produced by immunizing a mammal with a inoculum of the present invention and thereby induce in the mammal antibody molecules having the appropriate peptide immunospecificity. The antibody molecules are then collected from the mammal and isolated to the extent desired by well known techniques such as, for example, immunoaffinity chromatography. The antibody composition so produced can be used, inter alia, in the diagnostic methods and systems of the present invention to detect cells expressing N-CAM in a sample of tissue.

Monoclonal antibody compositions are also contemplated by the present invention. A monoclonal antibody composition contains, within detectable limits, only one species of antibody combining site capable of effectively binding a N-CAM homophilic peptide. Thus, a monoclonal antibody composition of the present invention typically displays a single binding affinity for a N-CAM homophilic peptide even though it may contain antibodies capable of binding proteins other than a N-CAM homophilic peptide.

Vectors which comprise the isolated nucleic acid molecule coding for a portion of N-CAM may be prepared by means well known to one skilled in the art. Suitable vectors comprise, but are not limited to, a plasmid or a virus. These vectors may be transformed into a suitable host cell to form a host cell vector system for the production of a N-CAM homophilic peptide. This invention further provides an isolated DNA or cDNA molecule described hereinabove wherein the host cell is selected from the group consisting of bacterial cells (such as *E. coli*), yeast cells, fungal cells, insect cells and animal cells. Suitable animal cells include, but are not limited to Vero cells, HeLa cells, Cos cells, CVI cells and various primary mammalian cells. Cos cells are transfected by the DEAE-Dextran method as follows: 80% confluent overnight cultures are transfected with 5 μg DNA, per 100 mm dish, in 250 μg/ml DEAE Dextran (Pharmacia), 100 mM Tris pH 7.3, in DMEM. After 6 h cells are washed and incubated in DMEM 10% calf serum, 0.1 mM chloroquine (Sigma) for 2.5 h, followed by incubation in DMEM 10% calf serum overnight. For isolation of peptide the medium is changed to OPTI-MEM (BRL), and the cells are incubated for 48 h.

Methods for facilitating the transport of drugs across the blood-brain barrier are known (see, for example Bickel, U. et al. (1993) *Proc. Natl. Acad. Sci. USA* 90 2618–2622). Suitable brain transport vectors include proteins such as cationized albumin or the OX26 monoclonal antibody to the transferrin receptor.

EXAMPLE 1

Purified N-CAM Inhibits Astrocyte Proliferation

Addition of N-CAM purified from rat forebrain to primary cultures of astrocytes (at a density of $7\times10^4$ cells/cm$^2$) in chemically defined medium (SFM) inhibited their proliferation in a concentration dependent manner (FIG. 1A).

Astrocyte Cultures

Primary cultures of astrocytes were prepared from the forebrains of 4–5 day old neonatal rats. After decapitation and removal of the forebrains from the skull, the meninges were carefully peeled off, and forebrain tissue was triturated in sterile phosphate buffered saline (PBS) using firepolished pipettes. The resulting suspension of tissue fragments was incubated in Hank's balanced salt solution (Gibco BRL) with 2.5 mg/ml trypsin, 1 mM EDTA and 0.1 mg/ml DNase (Boehringer) at 37° C. for 15 minutes. Undissociated tissue was removed by centrifugation and the remaining cell suspension was centrifuged through a cushion of 3.5% bovine serum albumin to remove cell debris. The pellet was resuspended in serum free medium (SFM) consisting of Dulbecco's Modified Eagle Medium (D-MEM), 2 mM L-glutamine, 50 U/ml penicillin G sodium and 50 μg/ml streptomycin sulfate (all from Gibco BRL) supplemented by 10% (vol/vol) fetal bovine serum (FBS). The cells were transferred to a standard 100 mm tissue culture dish (Falcon) and incubated at 37° C. for 1–2 hours. After mild shaking, the supernatant containing unattached cells was transferred to a 100 mm collagen-coated dish. Cultures were maintained in SFM supplemented with 10% FBS in 5% $CO_2$/95% air for about 7 days before the start of an experiment. Cell samples were checked regularly for the expression of GFAP, a marker for astrocytes. Only those cultures containing more than 95% astrocytes were used.

Purification of N-CAM

N-CAM was purified from early postnatal rat brains by affinity chromatography using a cross-reactive monoclonal anti-human N-CAM antibody (a generous gift of Dr. John Hemperly, Becton Dickinson Research Center, Research Triangle Park, N.C.). Purity of the preparations was tested by SDS gel electrophoresis using standard Coomassie blue staining and Western blotting techniques. Protein concentrations were estimated using the Bio Rad Micro Bradford assay. In some experiments, purified N-CAM was treated with 1 U/ml neuraminidase (from *Vibrio cholerae,* Calbiochem) in 100 mM sodium acetate, 2 mM $CaCl_2$, 2 mM EDTA, for 24 hours at 35° C. and pH=5.5 (Hoffman, S. et al. (1984) *Proc. Natl. Acad. Sci. USA* 81, 6881–6885) before being added to cell cultures. SDS gel electrophoresis revealed that the purified N-CAM consisted mainly of the polysialylated embryonic form of N-CAM (MW 200–250 kD) with other molecular forms including an approximately 65 kD hydrolyzed N-CAM fragment present in lower amounts.

Proliferation Assay

Astrocytes were labeled by addition of 10 μl 8.72 μM [$^{35}$S]-L-methionine (New England Nuclear, approximately 1200 Ci/mmol) to 10 ml culture medium and transferred into 96-well plates (Falcon) usually at a density of $2\times10^5$ cells/ml (equivalent to $7\times10^4$ cells/cm$^2$ or $2\times10^4$ cells/well). After cell attachment, the culture medium was exchanged for SFM. In antisense experiments, oligonucleotides were added at the same time (T=0). Growth factors, purified N-CAM, or synthetic peptides were added after the cells had remained in SFM for 48 hours (T=48); at this time most of the cells are synchronized with respect to their position in the cell cycle at $G_1/G_0$ (Kniss and Burry, 1988). After another 12 hours (at T=60), [$^3$H]-thymidine (New England Nuclear, 20 Ci/mmol) was added (0.38 μM, 10 μCi/ml). Following an additional 12 hours (T=72), the wells were drained, counts precipitated by ice-cold 10l trichloroacetic acid, and the plates left to dry. Counts were solubilized overnight by adding 100 μl 1 N KOH to each well, neutralized with 100 μl 1 N HCl, transferred to liquid scintillation vials and counted in 3 ml of Beckman Ready Safe liquid scintillation cocktail on a Packard 1600 TR counter. To determine levels of [AH]-thymidine incorporation relative to the number of cells, a dual dpm counting protocol was used (Crossin, K. L. (1991) *Proc. Natl. Acad. Sci. USA* 88, 11403–11407), which minimizes the overlap between the $^3$H and 35S energy spectra and takes into account detection efficiencies for both isotopes. In this paper, proliferation is expressed as [$^3$H]-thymidine incorporation normalized to [35]-methionine incorporation and calculated as [$^3$H] dpm/[35] dpm.

As shown by testing three separate preparations of rat N-CAM, maximal (>90%) suppression of proliferation could be effected at concentrations of 10 μg/ml (FIG. 1A). N-CAM in a concentration of about 0.2 μg/ml to about 2 μg/ml was sufficient for half-maximal (50%) suppression. Similar effects were observed after the addition of N-CAM purified from embryonic chick brain, which has been shown to bind to rodent N-CAM (Hoffman et al., 1984) also inhibited proliferation. At an N-CAM concentration of 10 μg/ml the cells tended to assume a somewhat rounded appearance; at concentrations ≦2 μg/ml (a range that still exhibited substantial inhibitory activity) no gross changes in cell morphology could be observed.

The addition of 1% FBS (containing various growth factors) and 20 ng/ml basic fibroblast growth factor (bFGF, Upstate Biotechnology Incorporated) to astrocyte cultures led to a marked increase in proliferation as compared to cultures in SFM (285±24% for FBS, n=14, and 347±56% for bFGF, n=12). Addition of N-CAM together with either 1k FBS or 20 ng/ml bFGF elicited also a suppressive effect similar in magnitude to that observed in SFM (FIG. 1B, C). Addition of 2 μg/ml N-CAM treated with neuraminidase to remove sialic acid produced an inhibitory effect comparable to untreated N-CAM (24±4% [$^3$H]-thymidine incorporation vs. SFM control, n=2).

EXAMPLE 2

Contact inhibition and Dependence of N-CAM Effect on Cell Density

Figure 2A:
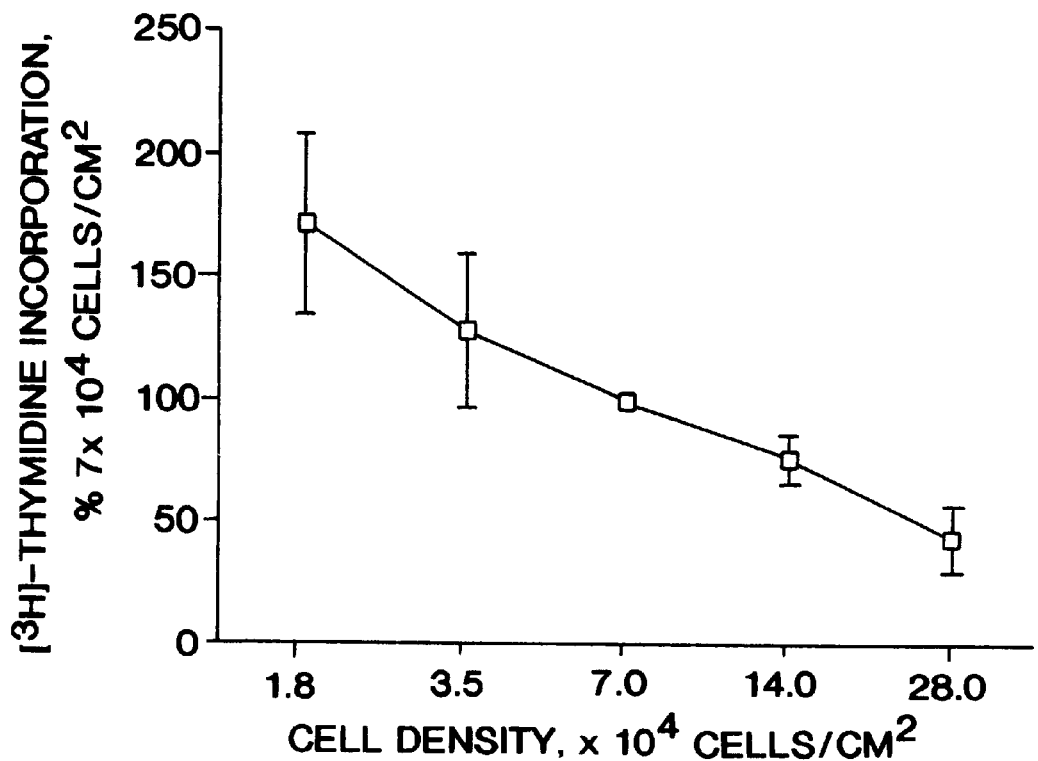
FIG. 2: Dependence of baseline proliferation levels (A) and inhibition of proliferation by 2 μg/ml N-CAM (B) on cell density. In (A), results are expressed as percent [$^3$H]-thymidine incorporation relative to a density of $7 \times 10^4$ cells/cm$^2$ (the density used in all other experiments) (B) shows the [$^3$H]-thymidine incorporation expressed as percent of the baseline (control) proliferation level (see A) for the corresponding cell density. n=5 throughout.
Figure 2B:
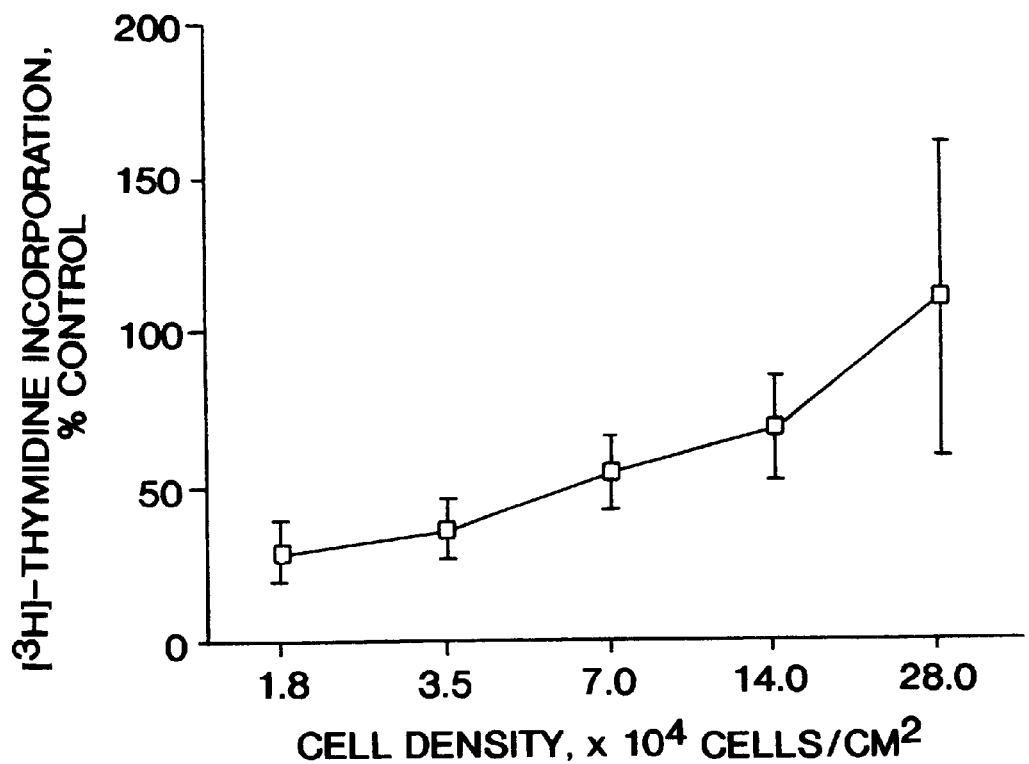

Astrocytes growing in SFM showed different levels of proliferative activity depending on their cell density. Levels of [$^3$H]-thymidine incorporation per cell were high at low cell densities, while confluent or nearly confluent cultures proliferated more slowly (presumably due to the phenomenon of "contact inhibition", FIG. 2A). When N-CAM was added to these cultures, the inhibitory effect of N-CAM on proliferation was critically dependent on cell density and thus on baseline proliferative activity. Inhibition was maximal at lower cell density ($1.8 \times 10^4$ cells/cm$^2$) when cells are actively proliferating, while N-CAM was virtually ineffective at higher cell densities ($28 \times 10^4$ cells/cm$^2$) when cultures are confluent.

It is unlikely that N-CAM added in solution acts by disrupting cell-cell adhesion itself given the observation that the effect is maximal at low cell density. The finding that N-CAM becomes progressively less effective in inhibiting proliferation as cell density rises may be because baseline proliferation levels of cells in confluent culture are already low and therefore cannot be suppressed further. The quiescence of confluent cultures could also be due in part to an autocrine effect via secretion of an inhibitory substance into the culture medium (e.g. Nieto-Sampedro, M. & Broderick, J. T. (1989) *J. Neurosci. Res.* 22, 28–35).

EXAMPLE 3

Anti-Proliferative Activity of Peptides

Several synthetic N-CAM homophilic peptides were added to astrocyte cultures.

Peptide Synthesis

Peptides were synthesized on a Gilson AMS-422 automated peptide synthesizer. The lyophilized peptides were resuspended in water, desalted and re-lyophilized at least once before use. Purity and concentrations of synthetic peptides were confirmed using mass spectrometry, analytical high pressure liquid chromatography (HPLC) and amino acid analysis.

Figure 3:
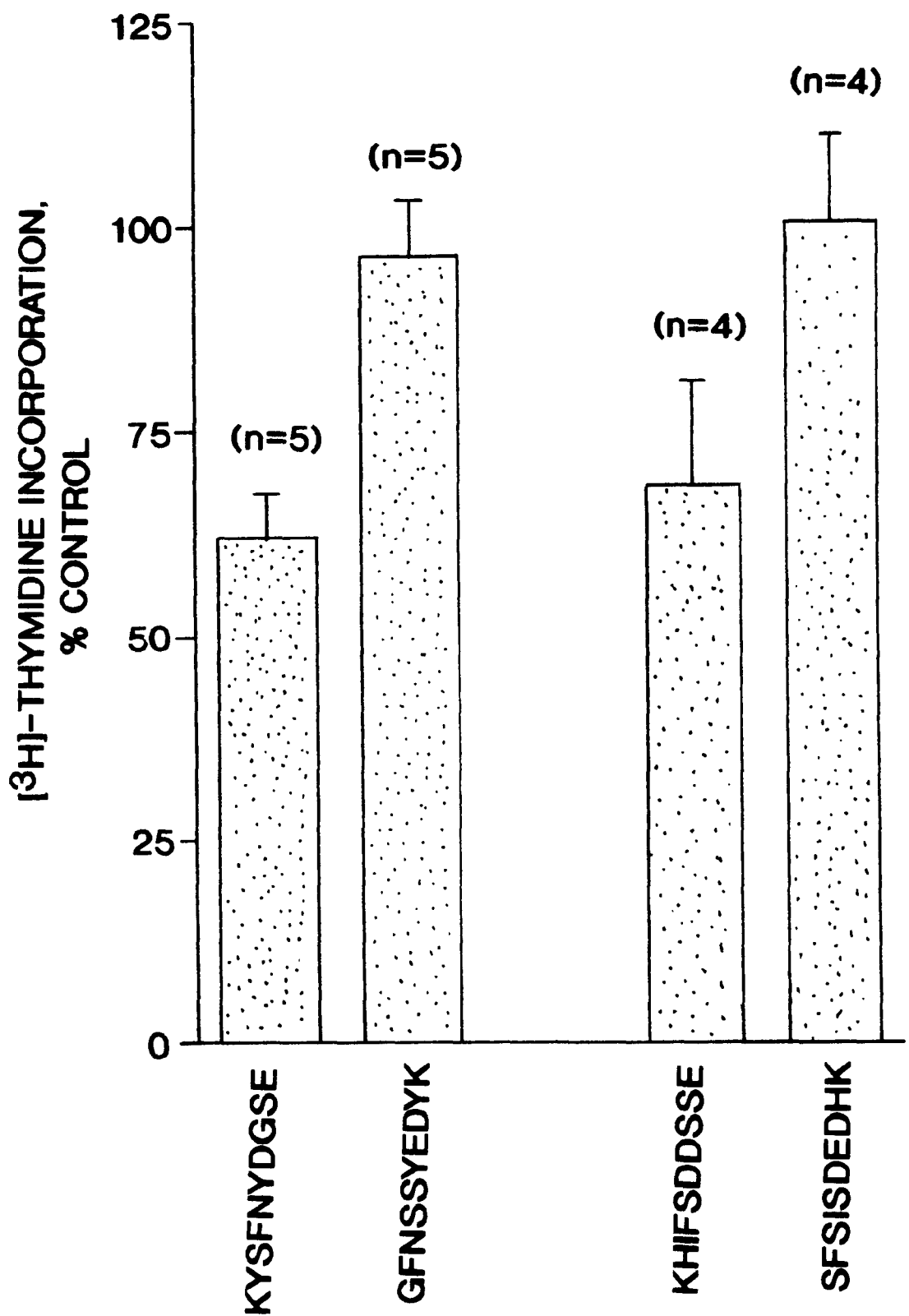
FIG. 3: Inhibitory effect of synthetic peptides with sequences containing a putative N-CAM homophilic binding site. Peptides are added at 0.1 mg/ml to SFM, with astrocytes at a density of $7 \times 10^4$ cells/cm$^2$. From left to right: chick N-CAM peptide and corresponding random peptide, rat N-CAM peptide and corresponding random peptide.

At a concentration of 0.1 mg/ml, the peptide KYS-FNYDGSE (SEQ ID NO 1), identical to an N-CAM homophilic binding region located in the third immunoglobulin-like domain of chick N-CAM, inhibited proliferation, while a peptide of the same length and amino acid composition but with randomized sequence (GFNSSYEDYK) (SEQ ID NO 8) had no effect (FIG. 3). The direct homologue to the chick peptide for rat N-CAM, KHIFSDDSSE (SEQ ID NO 2), had a similar inhibitory effect, while the corresponding random peptide SFSISD-EDHK (SEQ ID NO 9) did not affect proliferation.

EXAMPLE 4

Partial Reversal of the Inhibition of Proliferation After Adding Antisense Oligonucleotides The amounts of N-CAM present in astrocytes were quantified by Western blotting. Cultures were grown as described and cellular material was lysed in buffer (phosphate buffered saline, pH 7.4, containing 0.5% NP-40, 350 µg/ml PMSF, 2 µg/ml aprotinin, 0.5 µg/ml leupeptin, and 0.7 µg/ml pepstatin A) at 4° C. Standard Western blotting techniques were employed either using cell lysate directly or after N-CAM immunoprecipitation. [$^{125}$I]-Immunolabeled N-CAM was estimated by densitometry on a Molecular Dynamics PhosporImager using ImageQuant software.

Phosphorothioate oligoribonucleotides were synthesized on an Applied Biosystems Model 380B DNA synthesizer using phosphoramidite chemistry. Two sequences of length 24 were used: one sequence 5'-AGAUCCUUAG WUCGCAGCAUUGUA-3' (SEQ ID NO 3) was complementary to position 205 to 228 of rat N-CAM, starting 4 bases before the translation initiation codon (Small, S. J., Shull, G. E., Santoni, M. J. & Akeson, R. (1987) *J. Cell Biol.* 105, 2335–2345) ("N-CAM antisense", another sequence 5'-GUCCAUGUACAUCUAGUCAGUUGA-3 (SEQ ID NO 10), consisted of the same nucleotides arranged in random order ("random antisense"). After deprotection, the oligonucleotides were purified using HPLC, ethanol precipitated, solubilized in distilled water and added to the culture medium at the indicated concentrations.

TABLE 1

Levels of N-CAM expression (sum of all molecular forms, mostly 140 kD and 120 kD, in % Control) in antisense experiments as determined by Western blotting. Data are expressed as mean ± S.E.M. (n) with n = number of experiments. *P < 0.02 vs. control (paired sample Student's t-test).

| Condition | N-CAM level |
|---|---|
| Control | 100 ± 0 (6) |
| +N-CAM antisense RNA | 65* ± 9 (5) |
| +random antisense RNA | 87 ± 18 (6) |

Figure 4:
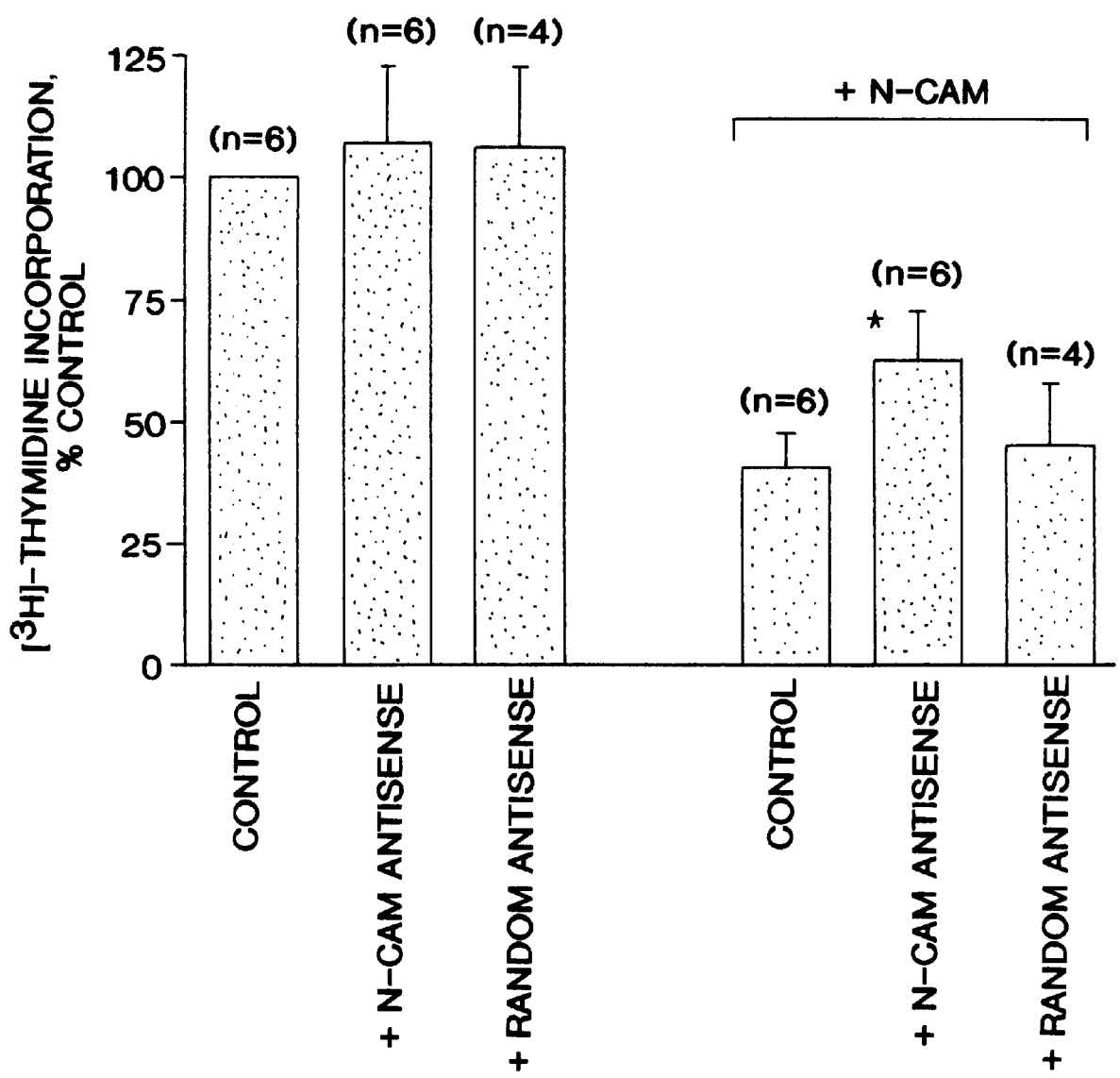
FIG. 4: Effect of N-CAM and random antisense oligonucleotides on the inhibition of glial cell proliferation by N-CAM. Left side (no N-CAM added): addition of 200 nM N-CAM antisense or random antisense oligonucleotides alone has no effect on proliferation. Right side (N-CAM added): SFM (Control) plus 2 μg/ml N-CAM produces inhibition, which is partially reversed by addition (48 hours prior to N-CAM) of 200 nM N-CAM antisense, but not by 200 nM random antisense oligonucleotides. * P<0.02 vs. Control+N-CAM (paired sample Student's t-test).

The addition of N-CAM antisense oligonucleotides for 48 hours resulted in significantly reduced N-CAM expression (P<0.02, Table 1). A random antisense oligonucleotide had, on average, no effect on N-CAM expression. Neither oligonucleotide led to changes in the gross morphology of astrocytes or had an influence on the baseline level of proliferation (FIG. 4, left). Addition of 2 µg/ml N-CAM to astrocyte cultures that had been preincubated with 200 nM N-CAM antisense oligonucleotides for 48 hours revealed a significantly (P<0.02) weaker inhibitory effect of N-CAM on proliferation (FIG. 4, right). Addition of N-CAM to astrocytes preincubated with the random antisense oligonucleotide revealed no such effect.

When the level of N-CAM expression by astrocytes is diminished by adding specific antisense oligonucleotides, the effect on proliferation elicited by N-CAM added to the medium is reduced. Because of the specificity of antisense probes, this finding suggests that expression of N-CAM on the glial cell surface is required for the inhibitory effect of soluble N-CAM and supports the notion that homophilic N-CAM binding mediates the decrease of astrocyte proliferation. Furthermore, addition of antisense oligonucleotides also reduces the effectiveness of the ongoing endogenous inhibition of glial proliferation caused by the neurons in the culture, having the net effect of enhancing the proliferation of glia and enriching the proportion of glial cells. The ability to obtain a culture enriched in glial cells is useful for experimental and testing purposes.

The antisense oligonucleotides were added to the culture medium at relatively low concentrations in order to reduce possible non-specific effects. For example, we found that oligonucleotide concentrations in the micromolar range reduced baseline proliferation levels irrespective of their sequence. Previous studies using antisense probes against bFGF in astrocyte cultures (Gerdes, W. et al. (1992) *Neu-* roReport 3, 43–46) have shown that phosphorothioate oligonucleotides can be effective within a few hours. In the present experiments, however, long incubation periods with N-CAM antisense oligonucleotides were required before significant reductions in N-CAM levels could be observed (see Perides, G., 1. et al. (1992) *Proc. Natl. Acad. Sci. USA* 89, 10326–10330); this may be due to slow N-CAM turnover rates (Friedlander, D. R., et al. (1985) *J. Cell Biol.* 101, 412–419). Even after 48 hours, only a gradual reduction in N-CAM levels was achieved. This finding would account for the significant but only partial reversal of the N-CAM effect on proliferation after N-CAM antisense oligonucleotide treatment.

EXAMPLE 5

In Vivo Effects on Glial Cell Proliferation

Experiments have shown the effectiveness in vivo of N-CAM and shorter peptides in reducing glial proliferation induced by lesions and brain trauma. Lesions were made by a hypodermic needle placed into the brain and N-CAM peptides or shorter fragments thereof were applied through the needle to the affected area.

Purification of Proteins and Peptides

The purification of N-CAM from early postnatal rat brains was done as described in Example 1 and the synthesis of peptides was done as described in Example 3. The recombinant protein Ig3, corresponding to the chicken N-CAM third Ig domain, was affinity purified on a column of monoclonal antibody CAM 1-Sepharose (Hoffman, S. et al., (1982) *J. Biol. Chem.* 257, 7720–7729. N-CAMs from different species bind with each other and the chicken clone was ready available. Hoffman, S. & Edelman, G. M. (1984) The mechanism of binding of neural cell adhesion molecules. In (Lauder, J. M. & Nelson, P., eds.). Plenum Press, New York, pp. 147–160.

Construction of N-CAM Expression Vectors

A peptide comprising the third Ig domain of chick N-CAM was produced recombinantly using an expression vector. The peptide, comprising $Val_{87}$ through $Lys_{180}$ of chick N-CAM, was produced by an expression vector constructed from a segment including nucleotides 259 to 540 of clone pEC 208 (Hemperly, et al. (1986) *Proc. Natl. Acad. Sci. USA* 83, 3037–3041). Clone pEC 208 was generated by PCR amplification, its DNA sequence was confirmed and it was inserted into the Nco I/Bam I sites of pET 3d (Novagen). PCR primers were chosen to amplify the region coding for the third Ig domain and add a Nco I 5' and a BamH I site 3' to the coding region. The sequence coding for the peptide is given by SEQ ID NO:4, the 3' BamH I primer by SEQ ID NO:5, and the 5' Nco I primer by SEQ ID NO:6. The PCR conditions were 60 mM Tris HCl, 15 mM NH4SO4, 2 mM $MgCl_2$, pH 9.5 (PCR Optimizer Buffer G, Invitrogen), 1 minute cycles at 95, 60 and 72° C.

The PCR product (SEQ ID NO:7) was digested with BamH I and Nco I, and ligated into a vector (pET-3d) that had been digested separately with BamH I and Nco I to form the expression vector. There are several suitable prokaryotic expression vectors, of these pET-3d is preferred. Suitable eukaryotic expression vectors include pNUT (Searle, P.F. et al. (1985) *Molec. & Cell. Biol.*5, 1480–1489) and pcDNAI neo (Invitrogen).

E. coli cells were transfected with the expression vector and cultured. Protein was extracted from the cultured cells, and the recombinant peptide was isolated by affinity purification using a CAM 6 (Hoffman, S. et al. (1982) *J. Biol. Chem.* 257, 7720–7729) monoclonal antibody column.

Stereotactic Placement of Lesions

Samples were injected into the brains of rats (Wistar Albino, Male, 200–250 g, Charles River, anesthetized with xylazine (12 mg/kg) and ketamine (90 mg/kg) through a 26 gauge needle. The needle point was placed at the stereotactic coordinates of either the hippocampus, cerebral cortex or striatum (Table 2). Bilateral injections of 3–4 μl were made using an Hamilton syringe. Each animal received an infusion of either the purified rat N-CAM (250 μg/ml), the third Ig domain of chicken N-CAM (5 mg/ml), or the rat N-CAM peptide KHIFSDDSSE (SEQ ID NO 2) (1 mg/ml) in PBS into one hemisphere; the other hemisphere was infused with the random peptide (SFSISDEDHK (SEQ ID NO 9), 1 mg/ml in PBS) as a control. The experimental and control sides varied between animals and choice of side had no significant effect on the results. Three μl of each protein or peptide was infused at a rate of 0.2 μl per minute after which the needle was left in place for 5 minutes and then removed. In one experiment, a group of animals received basic fibroblast growth factor (bFGF, 450 ng) in the solutions which contained either the random peptide or the purified N-CAM.

The samples were either purified N-CAM in phosphate buffered saline (PBS), N-CAM peptide KHIFSDDSSE (SEQ. ID. NO. 2) (1 mg/ml or 10 mg/ml) in PBS, or the corresponding random peptide SFSISDEDHK (SEQ ID NO 9) (1 mg/ml) (see Example 3 above). The injection rate was about 0.2 μl/min; the needle was left in place for 5 minute after the injection. Each animal received either the purified N-CAM or the N-CAM peptide injected into one side of the brain and the corresponding structure on the other side was injected with the random peptide as a control.

TABLE 2

Stereotactic Coordinates of Lesions (using bregma as a zero point)

| | Anterior-Posterior (AP) | Lateral (L) | Ventral (V, from dura) |
|---|---|---|---|
| Hippocampus: | -3.30 mm | +1.60 mm | -3.20 mm |
| Cerebral Cortex: (The needle entered the cerebral cortex at a 20 degree angle) | +0.70 mm | +2.70 mm | -1.60 mm |
| Striatum: | +0.70 mm | +2.60 mm | -4.70 mm |

Three animals were examined for each treatment and brain region described. Animals were maintained for a postinjection survival time of about 70–72 hours. During that time they received five injections of bromodeoxyuridine (Brdu) dissolved in 0.007 N NaOH (120 mg/kg, intraperitoneal). Two of the three animals that had been injected in the hippocampus received Brdu approximately 18, 28, 42, 52, and 70 hours after the stereotactic surgery. All of the animals that had been injected in the cerebral cortex or the striatum and one animal injected in the hippocampus received Brdu approximately 2, 18, 28, 42, and 52 hours after the stereotactic surgery.

Animals were perfused under anesthesia with about 30 ml of ice-cold PBS followed by about 400 ml of ice-cold 4-paraformaldehyde in PBS. The brains were then removed and postfixed for 2–16 hours in 4% paraformaldehyde in PBS then placed in succeeding solutions of ascending concentrations of sucrose (12%, 18%, and 24%). The brains were then sectioned on a cryostat at a thickness of 10 μm.

Immunocytochemistry

Hippocampal tissue

Non-specific binding on the sections was blocked by incubation in 8% fetal bovine serum (FBS) in PBS. Sections were then incubated in polyclonal antibody to glial fibrillary acidic protein (GFAP; 1:100 dilution, Dako) in 0.2% Triton X-100, 8% FBS/PBS for 24 - 48 hr at 4° C. The sections were processed using a biotinylated secondary antibody and the Vectastain ABC kit (Vector), and stained with a diaminobenzidine peroxidase substrate kit from Vector or Pierce. The sections were then incubated for 6 minutes in a solution of Proteinase K (Dako), rinsed and incubated in 2 N HCL for 20 minutes at 37° C. The sections were rinsed and blocked in 8% FBS/PBS and incubated in a monoclonal antibody to Brdu (1:40 dilution, Dako), 0.01% Triton X-100, 8% fetal bovine serum/PBS for 24–48 hr at 4° C. The sections were processed using a biotinlyated secondary antibody and the Vectastain ABC kit (Vector), and stained with a VIP peroxidase substrate kit from Vector giving the Brdu positive cells a red color. The sections were then rinsed in PBS and coverslipped in glycerol/PBS.

GFAP positive cells and cells positive for both GFAP and BRDU were counted under a Zeiss Axiophot light microscope. Three sections which contained the center of the lesion were examined for each animal. An area on either side of the lesion having a radius of about 600 μm was examined.

Cerebral Cortical and Striatal Tissue

The sections were incubated for 3 minutes in Proteinase K (Dako), rinsed and then incubated in 2 N HCL for 20 min at 37° C. The sections were rinsed and blocked in 8% FBS/PBS and incubated in a monoclonal antibody to Brdu (1:40 dilution, Dako), a polyclonal antibody to S100 (1:100 dilution, Dako or Sigma) in 0.3% Triton X-100 and 8% FBS/PBS for 3–4 hours at room temperature. A solution containing a FITC conjugated anti-mouse secondary antibody and a Texas red conjugated anti-rabbit secondary antibody (Vector) were then applied for 1 hour. The tissue was rinsed in PBS and coverslipped with SlowFade (Molecular Probes).

S100 immunoreactive cells and cells immunoreactive for both S100 and Brdu were counted under a Zeiss Axiophot fluorescent microscope using a filter whose bandwidth contained the excitation and emission wavelengths for FITC and Texas Red (Omega Optical). Three sections which contained the center of the lesion per animal were examined. Approximately 300 μm on either side of the lesion was examined.

TABLE 3

Labeling index after different treatments following a stab injury.

| Brain Region | Infusion (Experimental) | Labeling Index (Control) | Labeling Index (Experimental) | Percent Difference |
|---|---|---|---|---|
| Cerebral Cortex | N-CAM | 21.3 ± 1.2 | 10.2 ± 1.5 | −52.1 ± 4.5 |
|  | 3rd Ig Domain | 24.9 ± 2.9 | 13.9 ± 1.9 | −44.3 ± 9.4 |
|  | N-CAM Peptide | 18.9 ± 4.8 | 13.2 ± 3.8 | −30.4 ± 7.8 |
| Hippocampus | N-CAM | 19.6 ± 3.3 | 14.6 ± 2.3 | −25.2 ± 1.6 |
|  | 3rd Ig Domain | 18.4 ± 2.6 | 15.6 ± 2.2 | −15.0 ± 3.1 |
|  | N-CAM Peptide | 19.9 ± 2.1 | 14.5 ± 2.0 | −27.1 ± 2.9 |

TABLE 3-continued

Labeling index after different treatments following a stab injury.

| Brain Region | Infusion (Experimental) | Labeling Index (Control) | Labeling Index (Experimental) | Percent Difference |
|---|---|---|---|---|
| Striatum | N-CAM | 26.1 ± 0.7 | 20.7 ± 0.7 | −20.8 ± 2.1 |
|  | 3rd Ig Domain | 24.3 ± 5.2 | 19.6 ± 3.9 | −19.5 ± 5.1 |
|  | N-CAM Peptide | 19.1 ± 0.9 | 16.3 ± 0.9 | −14.5 ± 2.3 |

The data are presented as mean ± S.E.M., n = 3 for each condition. All comparisons of the labeling indicates between the N-CAM or N-CAM related molecules and the random peptide within each brain region were found to be significant ($p < 0.05$; paired sample Student's t-test).

Figure 5:
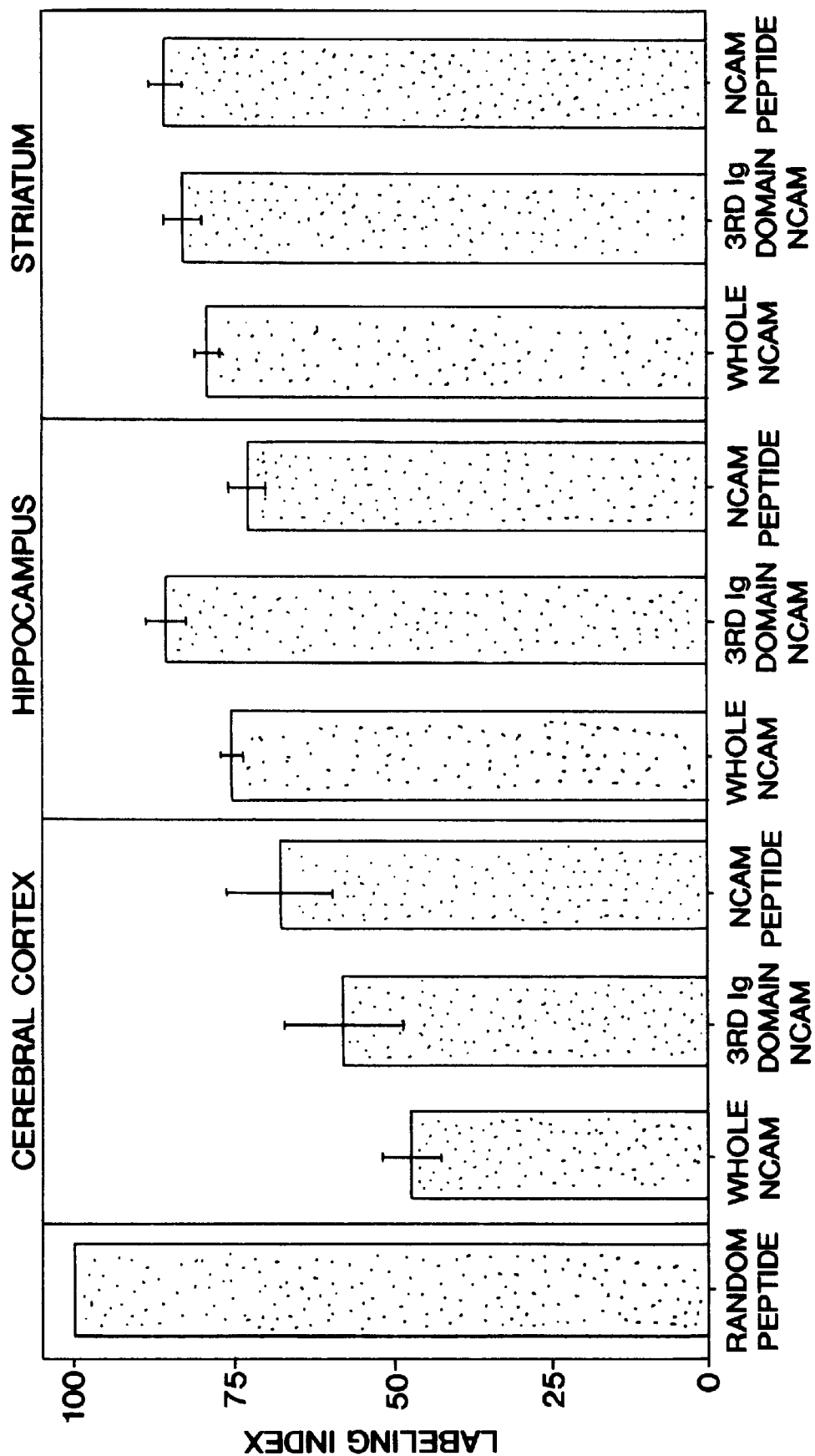
FIG. 5: The labeling index of dividing astrocytes infused with rat N-CAM, the third Ig domain of chicken n-CAM, or the peptide derived from the third Ig domain of rat N-CAM in the cerebral cortex, hippocampus, or striatum 3 days after the lesion (n=3 for each experimental condition; data are presented as mean ±S.E.M.) . The labeling index is defined as the percentage of labeled astrocytes (S100 or GFAP positive) that were also BrdU positive. For each brain region, the labeling index for the control condition (infusion of the random peptide) was set to 100%. In all cases, there were significantly fewer (p<0.05; paired sample Student's t-test) dividing astrocytes after infusion of N-CAM or related molecules as compared to the control condition.
Figure 6:
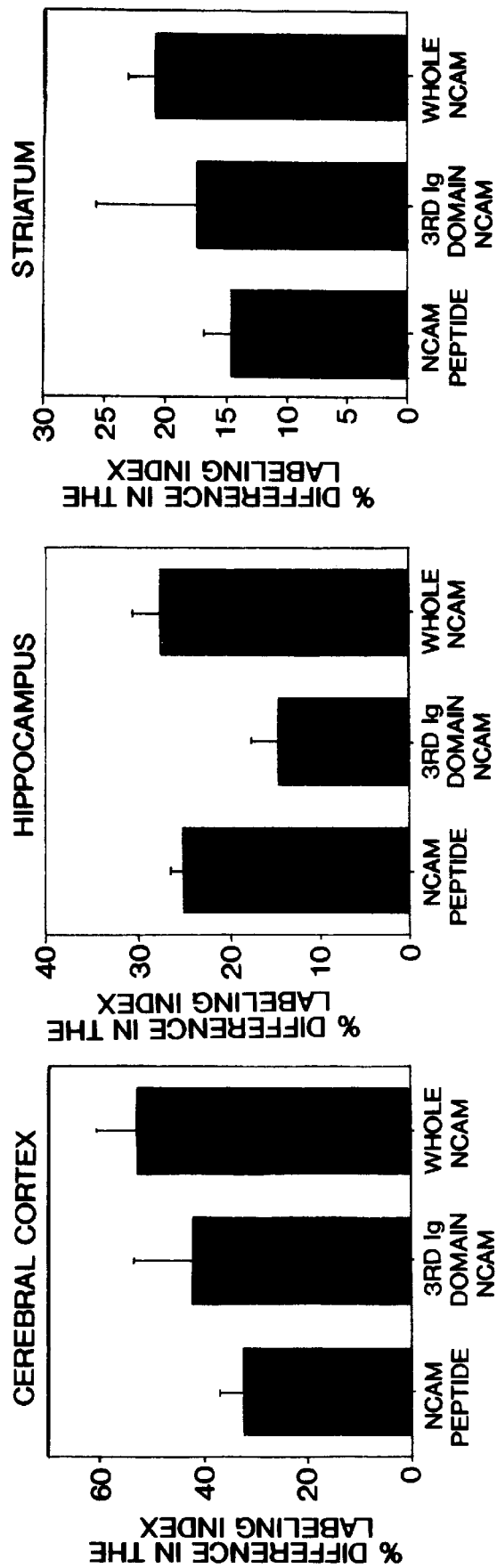
FIG. 6: Inhibition of glial cell proliferation by N-CAM peptides injected in vivo. Rats were lesioned with the needle of a Hamilton syringe and concomitantly injected with a N-CAM peptide into either the cerebral cortex (A), the hippocampus (B), or the striatum (C). The control peptide was injected into the corresponding site on the contralateral side of the brain. The rats then received five bromodeoxyuridine injections (intraperitoneal) over the following 72 hours. The percentage difference in labeling index is a reduction in astrocytes labeled with bromodeoxyuridine at the N-CAM peptide injection site compared to the contralateral control. Mean values ±S.E.M for three animals.

Analysis of the data showed that there was less glial proliferation at the injection sites for N-CAM, 250 μg/ml, the recombinant third Ig domain of chicken N-CAM (5 mg/ml) or the N-CAM KHIFSDDSSE (SEQ ID NO 2) peptide (1 mg/ml) than for the control random peptide SFSISDEDHK (SEQ ID NO 9). The results are summarized in Table 3 and FIGS. 5, 6 and 7.

Infusion of the whole N-CAM into the cerebral cortex at the lower dose of 100 μg/ml inhibited astrocyte proliferation by 0–10%; at 150 μg/ml, the inhibition ranged between about 4 to about 20%.

Figure 7:
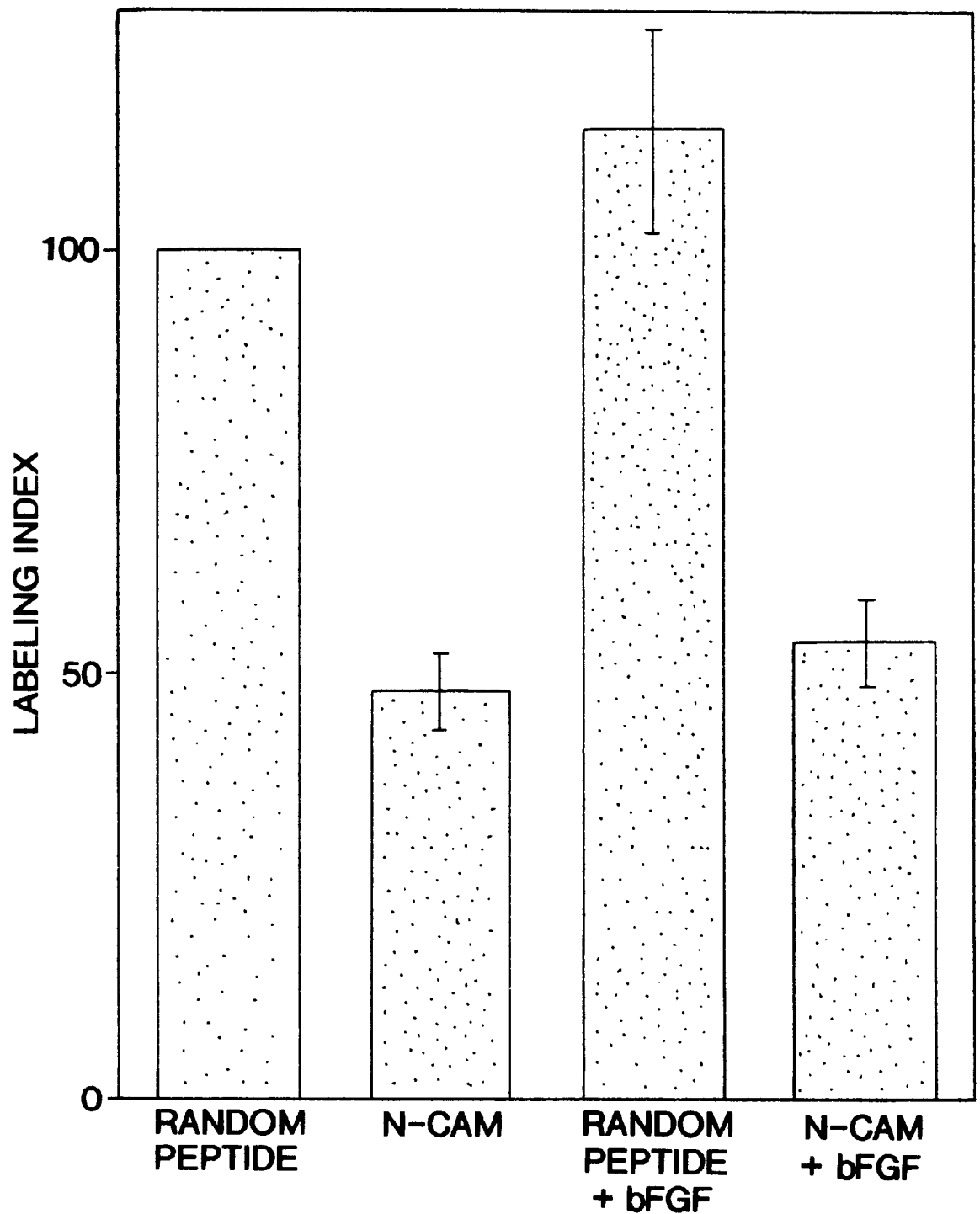
FIG. 7: The labeling index of dividing astrocytes 3 days after a cortical lesion infused with N-CAM, the control random peptide, bFGF plus N-CAM, or the random peptide plus bFGF (N=3 for each condition).

These results indicate that N-CAM partially inhibited astrocyte cell division in the three forebrain regions examined. Nevertheless, there was regional variability in the extent to which N-CAM or its related peptides can inhibit glial proliferation. The strongest effects (~50% inhibition) were seen in the cerebral cortex with smaller effects in the hippocampus and striatum. The variability between regions may be due to several factors. Astrocytes from different regions of the brain have been shown to have variable responses to injury. In addition, differences in the ability of the injected molecules to diffuse within a structure may contribute to this variation. Overall, the entire N-CAM molecule was the most efficacious in its ability to inhibit astrocyte proliferation even though it was injected at a lower concentration than the N-CAM peptide and the recombinant third Ig domain. The entire N-CAM molecule was also able to oppose the mitogenic effects of bFGF (FIG. 7). This is consistent with our previous studies on the inhibition of astrocyte proliferation by N-CAM in vitro.

Manipulation of the timing of N-CAM applications and of other reagents, such as glial cell proliferation inhibitors, may enhance the inhibition of proliferation. One useful approach would include insertion of a confined flow passageway, such as a hypodermic needle, catheter, permanent canula or the like, for supplying N-CAM, N-CAM peptides or antibodies intracranially, intraventricularly, into the subarachnoid space or directly to the site of the lesion. Such an approach could provide the N-CAM, N-CAM peptides or antibodies continuously or in multiple applications.

EXAMPLE 6

Antibodies Immunoreactive with N-CAM Are Capable of Suppressing Glial Cell Proliferation Polyclonal antibodies to N-CAM or their Fab' fragments also inhibited glial cell proliferation. Experimental conditions were the same as described in Example 1. Fab' fragments were prepared from anti-mouse N-CAM polyclonal antibodies as previously described (Brackenbury, R. et al. (1977) *J. Biol. Chem.* 252, 6835–6840).

Anti-mouse N-CAM polyclonal antibody (0.1 mg/ml) and Fab' fragments (0.03 mg/ml) prepared from this antibody exerted an inhibitory effect on astrocyte proliferation (53±15%, n=2, and 56±13%, n=4, respectively, vs. SFM).

EXAMPLE 7

Modulation of the Inhibition of Glial Cell Proliferation by Drugs

Figure 8:
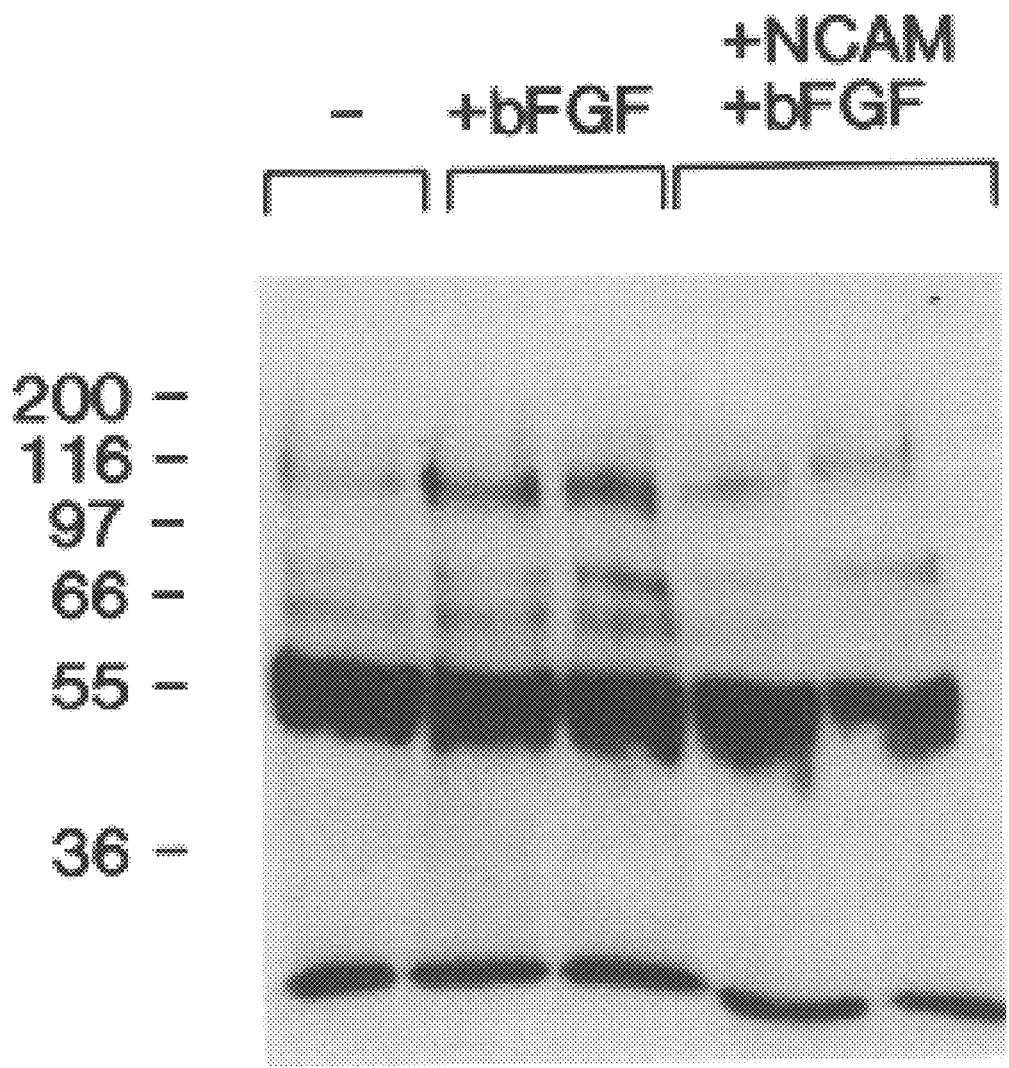
FIG. 8: An autoradiogram of an immunoprecipitation experiment showing that at least one protein in the molecular weight range of 60–70 kDa and one protein at approximately 120 kDa showed diminished tyrosine phosphorylation after N-CAM treatment.

The effects of drugs that affect particular signalling pathways were studied in the presence or absence of N-CAM to determine which pathways may have synergistic effects with N-CAM, or which agents may reverse the effects of N-CAM, are shown in FIG. 8 and Table 4. We focussed on three areas: (1) activation of tyrosine kinases and protein kinases A and C, (2) activation of calcium channels, and (3) activation of G proteins.

Immunoprecipitation

Astrocyte cells were seeded at a density of $7\times10^4/cm^2$ in a 100 mm tissue culture dish in Dulbecco's modified essential medium (DMEM) containing 10% fetal calf serum and gentamycin (5 μg/ml) at 37 degrees C with 7% $CO_2$. After overnight culture, the medium was replaced with serum-free medium and the cells are cultured for an additional 48 hr. The serum-starved cells were treated for 30 minutes in the presence of N-CAM (2 μg/ml) or buffer alone and then stimulated for 10 minutes with bFGF (100 ng/ml) to stimulate tyrosine phosphorylation through the FGF receptor.

Cells were solubilized in a lysis buffer composed of 50 mM tris-HCl, pH 7.4, 150 mM NaCl, 1.5 mM $MgCl_2$, 1.5 mM EGTA, 1 Triton X-100, phosphatase inhibitors (100 mM sodium fluoride, 30 mM p-nitrophenylphosphate, 10 mM sodium pyrophosphate, 500 AM sodium orthovanadate, 5 μM $ZnCl_2$), and protease inhibitors (10 μl/ml leupeptin, 10 μg/ml aprotinin, 1 mM PMSF). Cell lysates were immunoprecipitated either with 5 μg/ml anti-phosphotyrosine antibodies or 10 μg/ml of anti FGF receptor antibodies for 2 hrs. at 4° C. followed by a 30 minute addition of 5 mg protein A-Sepharose beads.

Immunoprecipitates were washed in tris-buffered saline (50 mM tris-HC1, pH 7.4, 150 mM NaCl) containing 0.2% Triton X-100, boiled in Laemmli sample buffer, and the proteins resolved on a 7% SDS-polyacrylamide gel and electrophoretically transferred to Immobilon membranes (Millipore, Bedford, Mass.). Duplicate samples for each immunoprecipitate were blotted with antibodies to phosphotyrosine and with the particular immunoprecipitating antibody.

Immunoblotting was performed by incubation with the indicated antibodies followed by $^{125}$I-labeled protein A; the resulting autoradiogram was exposed for 14 hr on XAR film at −70° C. or scanned on a Molecular Dynamics PhosphorImager (Sunnyvale, Calif.). The amount of reactivity with antibodies to phosphotyrosine relative to the amount of reactivity with antibodies to each specific protein can be calculated from imaging these gel blots, in extracts from N-CAM treated cells vs. non treated cells. This determines whether the FGF receptor or other proteins analyzed in this same paradigm are changed in their levels of tyrosine phosphorylation upon N-CAM treatment.

We found that several tyrosine kinase inhibitors completely blocked astrocyte proliferation, suggesting that the activity of at least one protein tyrosine kinase is required to sustain astrocyte proliferation. We examined differences in the patterns of tyrosine phosphorylated proteins between proliferating astrocytes and astrocytes treated with N-CAM. Astrocytes were treated with bFGF to stimulate tyrosine phosphorylation and cell proliferation with and without prior exposure to N-CAM. Cell extracts were then immunoprecipitated with anti-phosphotyrosine antibodies followed by immunoblots of the immunoprecipitated material with the same antibodies. These experiments indicated that at least one protein in the molecular weight range of 60–70 kDa and one protein at approximately 120 kDa (postulated to be the FGF receptor itself) showed diminished tyrosine phosphorylation after N-CAM treatment (FIG. 8). The strong band at 55 kDa is the heavy chain of the immuprecipitating Ig revealed with the second antibody and iodinated protein A.

Agents that stimulate or inhibit particular signalling pathways in the presence or absence of N-CAM can affect cell proliferation measured by thymidine incorporation (Table 4). We chose these agents based on their ability to activate or inhibit signalling pathways that have been implicated in the ability of N-CAM to support neurite outgrowth. They are grouped into agents that affect the activity of protein kinase A and protein kinase C, and agents that affect G proteins and calcium channels (Table 4).

The activation of protein kinase C (PKC) by phorbol (PMA) treatment led to a strong mitogenic response in astrocyte cultures. Conversely, the inhibition of protein kinase C with calphostin C, which is a highly specific inhibitor of protein kinase C, inhibits proliferation. This strongly suggests that astrocyte proliferation in vitro requires the activity of PKC. One effect of N-CAM might therefore be to decrease protein kinase C activity.

Activation of adenylate cyclase and protein kinase A by forskolin blocks proliferation of astrocytes in culture. The presence of K252b, a more general inhibitor of protein kinases A and C, allowed the astrocytes cells to grow normally in the presence of concentrations of N-CAM, which would otherwise inhibit cell proliferation. These results indicate that kinases other than PKC, e.g. PKA, may also be important in decreasing astrocyte proliferation. It is therefore possible that N-CAM inhibits proliferation by activating PKA and that K252b reverses this effect by its inhibition of PKA.

In contrast to these results and to those reported from experiments on neurons, we found that calcium channel blockers and arachidonic acid had no effect on the ability of N-CAM to inhibit astrocyte proliferation in culture. Activation of G proteins with mastoparan stimulated astrocyte proliferation and this was not inhibited by the concentration of N-CAM used, a concentration that inhibited glial proliferation to 54% of control in the absence of mastoparan (Table 4).

Inhibition of G proteins with pertussis toxin slightly inhibited astrocyte proliferation but N-CAM was still able to inhibit proliferation in the presence of pertussis toxin. These results are of interest since these agents that affect G proteins and calcium have been shown to inhibit the ability of N-CAM to support neurite outgrowth, but they showed minimal effects on N-CAM inhibition of astrocyte proliferation. Astrocyte proliferation and neurite outgrowth are two very different biological measurements, and these results indicate that N-CAM may activate different signalling pathways in these different cell types.

TABLE 4

Components of N-CAM signalling pathways.
Numbers are mean ± S.E.M. for each condition. Additions
of N-CAM were 2 μg/ml, cell density was $2 \times 10^5$ cells/ml.
The control condition is serum-free medium (SFM) with no additions.

| Reagent | Mode of Action | Concentration | [$^3$H]-thymidine incorporation (% SFM Ctrl) | | | |
|---|---|---|---|---|---|---|
| | | | Drug alone | Drug + N-CAM | SFM Ctrl | SFM + N-CAM |
| PKC/PKA Activators/Inhibitors | | | | | | |
| PMA | PKC+ | 10 nM | 138 ± 16 | — | — | — |
| | | 100 nM | 268 ± 34 | 228 | 100 | 50 |
| Calphostin | PKC− | 0.1 μM | 111 ± 35 | — | — | — |
| | | 0.5 μM | 54 ± 35 | — | — | — |
| Forskolin | PKA+ | 1 μM | 73 ± 2 | — | — | — |
| | | 10 μM | 32 ± 6 | — | — | — |
| K252b | PKA−/ | 100 nM | 98 ± 17 | 85 ± 5 | 100 | 53 ± 8 |
| | PKC− | 200 nM | 78 ± 15 | 64 ± 1 | 100 | 43 ± 6 |
| G-Proteins, Calcium Channel Blockers | | | | | | |
| Mastoparan | Gprot+ | 50 μM | 213 ± 47 | 205 ± 30 | 100 | 54 ± 6 |
| Pertussis Toxin | Gprot− | .5 μg/ml | 74 ± 20 | 53 ± 9 | 100 | 50 ± 10 |
| | | 1 μg/ml | 67 ± 13 | 57 ± 13 | 100 | 49 ± 9 |
| ω-Conotoxin/diltiazem | Ca$^{++}$ channel blocker | 0.25 μM/ 10 μM | 94 ± 17 | 57 ± 9 | 100 | 64 ± 2 |
| Arachidonic Acid | | 10 μM | 107 ± 10 | 60 ± 12 | 100 | 52 ± 4 |

The effects of two drugs, mastoparan and methyl 2,5-dihydroxycinnamate, on glial cell proliferation inhibition of Ig3 were also examined. 2,5-dihydroxycinnamate (Calbiochem, San Diego, Calif.) is an erbstatin analogue that specifically decreases receptor-associated tyrosine kinase activity. The results (Table 5) indicate that Ig3 and N-CAM effects are altered in a similar way by these drugs.

TABLE 5

Drug Effects on Ig3 and N-CAM Glial Cell Proliferation Inhibition
Values are means of triplicate experiments. Additions of
N-CAM and Ig3 were 2 μg/ml, cell density was $2 \times 10^5$
cells/ml. The control condition is serum-free medium (SFM)
with no additions.

| % of SFM Medium Control | Drug Alone | Drug + N-CAM | Drug + Ig3 | N-CAM Alone | Ig3 Alone |
|---|---|---|---|---|---|
| Mastoparan (50 μM) | 210 | 202.5 | 192.5 | 32.5 | 30 |
| Methyl 2, 5-dihydroxycinnamate (0.25 μg/ml) | 65 | 60 | 59 | 34 | 31 |

EXAMPLE 8

Suppression of Glial Cell Proliferation by Monoclonal Antibodies Immunoreactive with N-CAM Glial cells and culture conditions were the same as used in Example 1. A mouse monoclonal antibody derived from clone N-CAM 16.2 was used. The antibody is an immunoglobulin type IgG$_{2b}$, directed against the third Ig domain of human brain N-CEM, and is commercially available as Anti-N-CAM 16 from Becton-Dickinson (San Jose, Calif.).

The monoclonal antibody was added to cultures as diluted ascites fluid at a final concentration of about 15 μg/ml. The antibody inhibited 60% of astrocyte proliferation.

The foregoing discussion and the accompanying examples are presented as illustrative, and are not to be taken as limiting. Still other variations within the spirit and scope of this invention are possible and will readily present themselves to those skilled in the art.

We claim:

1. A method of inhibiting proliferation of glial cells in vivo, the method comprising providing an intracranial confined flow passageway, and administering through said confined flow passageway a proliferation inhibiting amount of a N-CAM homophilic peptide having the amino acid sequence selected from the group consisting of KYSFNYDGSE (SEQ ID NO 1), KHIFSDDSSEE (SEQ ID NO 2) and the third immunoglobulin domain of N-CAM.

2. The method of claim 1 wherein said passageway comprises a hypodermic needle, a catheter, or a permanent canula.

3. The method of claim 1 further comprising repeating the administration with an amount sufficient for the inhibition of glial proliferation.

4. A method of inhibiting proliferation of glial cells in vivo, the method comprising providing an intraventricular confined flow passageway, and administering through said confined flow passageway a proliferation inhibiting amount of a N-CAM homophilic peptide having the amino acid sequence selected from the group consisting of KYSFNYDGSE (SEQ ID NO 1), KHIFSDDSSEE (SEQ ID NO 2) and the third immunoglobulin domain of N-CAM.

5. The method of claim 4 wherein said passageway comprises a hypodermic needle, a catheter, or a permanent canula.

6. The method of claim 4 further comprising repeating the administration with an amount sufficient for the inhibition of glial proliferation.

7. A method of inhibiting proliferation of glial cells in vivo, the method comprising providing a confined flow passageway into the subarachnoid space, and administering through said confined flow passageway a proliferation inhibiting amount of a N-CAM homophilic peptide having the amino acid sequence selected from the group consisting of KYSFNYDGSE (SEQ ID NO 1), KHIFSDDSSEE (SEQ ID NO 2) and the third immunoglobulin domain of N-CAM.

8. The method of claim 7 wherein said passageway comprises a hypodermic needle, a catheter, or a permanent canula.

9. The method of claim 7 further comprising repeating the administration with an amount sufficient for the inhibition of glial proliferation.

10. A method of inhibiting proliferation of glial cells in vivo, the method comprising providing a confined flow passageway directly to the site of proliferating glial cells, and administering through said confined flow passageway a proliferation inhibiting amount of a N-CAM homophilic peptide having the amino acid sequence selected from the group consisting of KYSFNYDGSE (SEQ ID NO 1), KHIFSDDSSEE (SEQ ID NO 2) and the third immunoglobulin domain of N-CAM.

11. The method of claim 10 wherein said passageway comprises a hypodermic needle, a catheter, or a permanent canula.

12. The method of claim 10 further comprising repeating the administration with an amount sufficient for the inhibition of glial proliferation.

13. The method of claim 10 wherein said proliferation results from a lesion or brain trauma.

14. A method of inhibiting proliferation of glial cells in a cell culture, the method comprising administering to said culture a proliferation inhibiting amount of a N-CAM homophilic peptide having the amino acid sequence selected from the group consisting of KYSFNYDGSE (SEQ ID NO 1), KHIFSDDSSEE (SEQ ID NO 2) and the third immunoglobulin domain of N-CAM.

15. The method of claim 14 wherein said cell culture is a mixed culture of glial and neural cells.

16. The method of claim 14 further comprising repeating the administration with an amount sufficient for the inhibition of glial proliferation.

17. The method of claim 14 further comprising a glial cell proliferation inhibitor.

18. The method of claim 17 wherein the glial cell proliferation inhibitor is calphostin.

19. The method of claim 17 wherein the glial cell proliferation inhibitor is forskolin.

20. The method of claim 17 wherein the glial cell proliferation inhibitor is pertussis toxin.

21. A composition suitable for inhibiting proliferation of glial cells and consisting essentially of a proliferation inhibiting amount of a N-CAM homophilic peptide having the amino acid sequence selected from the group consisting of KYSFNYDGSE (SEQ ID NO 1), KHIFSDDSSEE (SEQ ID NO 2) and the third immunoglobulin domain of N-CAM, and a glial cell proliferation inhibitor in a physiologically acceptable vehicle.

22. The composition of claim 21 wherein the glial cell proliferation inhibitor is calphostin.

23. The composition of claim 21 wherein the glial cell proliferation inhibitor is forskolin.

24. The composition of claim 21 wherein the glial cell proliferation inhibitor is pertussis toxin.

25. A composition suitable for inhibiting proliferation of glial cells wherein the composition contains a proliferation inhibiting amount of a N-CAM homophilic peptide having the amino acid sequence KHIFSDDSSEE (SEQ ID NO 2) in a physiologically acceptable vehicle.

* * * * *

UNITED STATES PATENT AND TRADEMARK OFFICE
CERTIFICATE OF CORRECTION

PATENT NO : 5,985,822
DATED : November 16, 1999
INVENTOR(S) : Edelman, et al.

It is certified that error appears in the above-identified patent and that said Letters Patent is hereby corrected as shown below:

In Column 1, line 14, please delete "HD09635" and insert --HL09635--

Signed and Sealed this

Nineteenth Day of September, 2000

Attest:

Q. TODD DICKINSON

Attesting Officer

Director of Patents and Trademarks